United States Patent
Kobayashi (10) Patent No.: US 10,335,575 B2
(45) Date of Patent: Jul. 2, 2019

(54) MEDICAL ELONGATED BODY

(71) Applicant: TERUMO KABUSHIKI KAISHA, Shibuya-ku, Tokyo (JP)

(72) Inventor: Junichi Kobayashi, Cupertino, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 455 days.

(21) Appl. No.: 14/921,397

(22) Filed: Oct. 23, 2015

(65) Prior Publication Data
US 2016/0082225 A1 Mar. 24, 2016

Related U.S. Application Data

(63) Continuation of application No. PCT/JP2013/062358, filed on Apr. 26, 2013.

(51) Int. Cl.
*A61M 25/01* (2006.01)
*A61M 25/00* (2006.01)
*A61B 1/005* (2006.01)

(52) U.S. Cl.
CPC .... *A61M 25/0138* (2013.01); *A61M 25/0013* (2013.01); *A61M 25/0051* (2013.01); *A61B 1/005* (2013.01); *A61M 2025/0059* (2013.01)

(58) Field of Classification Search
CPC .......... A61B 1/005; A61M 2025/0059; A61M 25/0013; A61M 25/0051; A61M 25/0138
See application file for complete search history.

(56) References Cited

U.S. PATENT DOCUMENTS

| 6,053,922 A | 4/2000 | Krause et al. |
| 6,273,876 B1 | 8/2001 | Klima et al. |
| 2003/0105415 A1 | 6/2003 | Mirigian |

(Continued)

FOREIGN PATENT DOCUMENTS

| CN | 1193899 A | 9/1998 |
| JP | 11-509752 A | 8/1999 |

(Continued)

OTHER PUBLICATIONS

International Search Report (PCT/ISA/210) dated Jul. 30, 2013, by the Japanese Patent Office as the International Searching Authority for International Application No. PCT/JP2013/062358.

(Continued)

*Primary Examiner* — Imani N Hayman
(74) *Attorney, Agent, or Firm* — Buchanan Ingersoll & Rooney PC (57) ABSTRACT

A medical elongated body is disclosed, which can improve the operability by suppressing anisotropy of torque transmission performance in accordance with the rotational direction while maintaining flexibility. The medical elongated body has a proximal shaft, which extends in an axial center direction and includes at least a part of which a spiral slit is formed. The proximal shaft includes a site in which the spiral inclination angles, which are angles in an extending direction of a spiral of the slit with respect to a cross-section orthogonal to the axial center direction, are different from each other, and a stepped portion in which the angle of the slit changes locally with respect to the spiral inclination angle is formed on one opposed surface constituting the slit, and an abutting portion on which the stepped portion abuts when the proximal shaft is twisted.

19 Claims, 5 Drawing Sheets

(56) References Cited

U.S. PATENT DOCUMENTS

2008/0287786 A1  11/2008  Lentz
2010/0274270 A1  10/2010  Patel et al.

FOREIGN PATENT DOCUMENTS

| | | |
|---|---|---|
| JP | 2000-197704 A | 7/2000 |
| JP | 2005-511259 A | 4/2005 |
| JP | 2010-527258 A | 8/2010 |
| WO | WO 97/03611 A1 | 2/1997 |
| WO | WO 03/051446 A1 | 6/2003 |
| WO | WO 2008/143858 A2 | 11/2008 |

OTHER PUBLICATIONS

Office Action (Notification of Reasons for Refusal) dated Jul. 19, 2016, by the Japanese Patent Office in corresponding Japanese Patent Application No. 2015-513455, and an English Translation of the Office Action. (10 pages).

Extended European Search Report dated Jan. 24, 2017, issued by the European Patent Office in corresponding European Application No. EP 13883257.1 (7 pages).

Office Action (First Office Action) dated Jun. 16, 2017, by the State Intellectual Property Office of People's Republic of China in corresponding Chinese Patent Application No. 201380076005.6, and an English translation of the Office Action. (10 pages).

Office Action dated Nov. 15, 2018 in corresponding European Patent Application No. 13 883 257.1.

MEDICAL ELONGATED BODY

CROSS-REFERENCES TO RELATED APPLICATIONS

This application is a continuation of International Application No. PCT/JP2013/062358 filed on Apr. 26, 2013, the entire content of which is incorporated herein by reference.

TECHNICAL FIELD

The present disclosure relates to a medical elongated body, which is inserted into a biological lumen, for example, a blood vessel.

BACKGROUND DISCUSSION

In recent years, treatment of a site on which it is difficult to perform a surgical operation, for example, percutaneous transluminal coronary angioplasty (PCTA), or treatment for minimum invasion into a human body has been performed using a catheter. In such a treatment, a guide wire is percutaneously inserted into a biological lumen, for example, a blood vessel, a catheter is pushed along the guide wire while the guide wire is advanced, and a distal portion of the catheter is induced to a target site, to perform treatment using a catheter. Accordingly, it can be necessary for the catheter to be flexibly bent along the shape of the lumen in the biological lumen. For this reason, a method (for example, refer to JP-T-2010-527258) of forming a spiral slit on an elongated tubular body constituting a shaft of a catheter has been known for the purpose of increasing flexibility of the catheter.

However, when a spiral slit is formed on a tubular body constituting a shaft of a catheter, torque transmission performance in accordance with a rotational direction varies due to anisotropy of the structure, and therefore, the operability of the catheter can be reduced. For example, torque acts in a direction, in which the gap of the slit is closed, when a proximal portion of a catheter is rotated on one direction side, whereas torque acts in a direction, in which the gap of the slit is opened, for example, a direction, in which the spiral is released, when the proximal portion of the catheter is rotated on the opposite direction side thereof. Slits cannot be closed more than the width of the gap of the slit in a case where torque acts in the direction in which the gap of the slit is closed, and therefore, the torque can be favorably transmitted. In contrast, the gap of the slit is opened more than necessary in a case where torque acts in a direction in which the gap of the slit is opened, and therefore, the torque cannot be favorably transmitted, thereby easily reducing the operability.

SUMMARY

The present disclosure has been made in order to solve the above-described problem. A medical elongated body is disclosed, which can improve the operability by suppressing anisotropy of torque transmission performance in accordance with the rotational direction while maintaining flexibility.

In a first exemplary embodiment, a medical elongated body is disclosed having a tubular body, which extends in an axial center direction and in at least a part of which a spiral slit is formed, in which the tubular body includes a site in which the spiral inclination angles, which are angles in an extending direction of a spiral of the slit with respect to a cross-section orthogonal to the axial center direction, are different from each other, and a stepped portion in which the angle of the slit changes locally with respect to the spiral inclination angle is formed on one opposed surface side of a pair of opposed surfaces constituting the slit, and an abutting portion on which the stepped portion abuts when the tubular body is twisted in a direction in which the spiral of the slit is released is formed on the other opposed surface side of the opposed surfaces, and in which the length of stepped portion in the axial center direction in a site in which the spiral inclination angle is relatively large is formed to be longer than that in a site in which the spiral inclination angle is relatively small.

In a second exemplary embodiment, a medical elongated body is disclosed having a tubular body, which extends in an axial center direction and includes at least a part of which a spiral slit is formed, in which the tubular body includes a site in which the spiral inclination angles, which are angles in an extending direction of a spiral of the slit with respect to a cross-section orthogonal to the axial center direction, are different from each other, and a stepped portion in which the angle of the slit changes locally with respect to the spiral inclination angle is formed on one opposed surface side of a pair of opposed surfaces constituting the slit, and an abutting portion on which the stepped portion abuts when the tubular body is twisted in a direction in which the spiral of the slit is released is formed on the other opposed surface side of the opposed surfaces, and in which the positions of at least two stepped portions, which are provided in the adjacent slits and are aligned in the axial center direction of the tubular body while drawing a spiral, are different in a circumferential direction of the tubular body.

In a third exemplary embodiment, a medical elongated body is disclosed having a tubular body, which extends in an axial center direction and includes at least a part of which a spiral slit is formed, in which the tubular body includes a site in which the spiral inclination angles, which are angles in an extending direction of a spiral of the slit with respect to a cross-section orthogonal to the axial center direction, are different from each other, and a stepped portion in which the angle of the slit changes locally with respect to the spiral inclination angle is formed on one opposed surface side of a pair of opposed surfaces constituting the slit, and an abutting portion on which the stepped portion abuts when the tubular body is twisted in a direction in which the spiral of the slit is released is formed on the other opposed surface side of the opposed surfaces, and in which the stepped portion is parallel to the axial center direction of the tubular body.

In the first exemplary embodiment of the medical elongated body which has been constituted as described above, with the provision of a site in which the spiral inclination angles of slits are different from each other, the operability of the medical elongated body can be improved by arbitrarily setting flexibility in accordance with the position in the axial center direction. In addition, a stepped portion and an abutting portion, which abut on each other when the medical elongated body is twisted in a direction in which a spiral is released, are provided in a slit, and therefore, release of a gap of the slit when the medical elongated body is twisted in a direction in which the spiral is released is suppressed. Furthermore, the lengths of the stepped portions in the axial center direction in a site in which the spiral inclination angle of the slit is relatively large are formed longer than those in a site in which the spiral inclination angle of the slit is relatively small. Therefore, it can be difficult for the stepped portions to come off from abutting portions since the lengths of the stepped portions become longer as in a site in which the caught state of a stepped portion with respect to an abutting portion is easily released due to a large spiral inclination angle of the slit. Therefore, the operability can be improved by suppressing anisotropy of torque transmission performance in accordance with the rotational direction.

If the local variation in the angle of the slit in the stepped portion is made to exceed 90 degrees, the stepped portion becomes easily caught by the abutting portion when the medical elongated body is twisted in a direction in which the spiral of the slit is released, and therefore, excessive twisting can suppressed.

In accordance with an exemplary embodiment, if the range of the inclination angle of the stepped portion with respect to the axial center direction is made to be within ±5 degrees, the stepped portion becomes substantially parallel to the axial center direction, and the stepped portion, which is provided on a side which is convexly curved when the tubular body is curved, for example, a side on which the width of the slit is widened, can move relatively to the abutting portion and becomes easy to return to its original position. For this reason, the flexural rigidity of the tubular body can be suppressed from becoming locally large due to the failure of the movement of the stepped portion to the abutting portion, and therefore, favorable flexibility can be provided.

In accordance with an exemplary embodiment, if the width of the gap of the slit is made to become constant, the shape of a stepped portion, which is formed to protrude from one opposed surface of a pair of opposed surfaces constituting the slit, and the shape of an abutting portion, which is formed on the other opposed surface of the opposed surfaces so as to abut on the stepped portion, become substantially the same as each other. For this reason, a stepped portion becomes easily caught by an abutting portion on an opposed surface when the tubular body is twisted in a direction in which the spiral of the slit is released, and therefore, excessive twisting can be reliably suppressed.

In accordance with an exemplary embodiment, if the positions of the stepped portions which are provided in the adjacent slits and are aligned in the axial center direction of the tubular body while drawing a spiral, are made to be different in a circumferential direction of the tubular body, the stepped portions of the adjacent slits do not overlap each other in the axial center direction of the tubular body, and it can be difficult for the flexural rigidity of the tubular body to be deviated depending on the circumferential direction position. Therefore, favorable flexibility can be provided.

In accordance with an exemplary embodiment, if the tubular body has a site in which the spiral inclination angle gradually changes and the lengths of the plurality of stepped portions which are provided in the site in the axial center direction are made to gradually become longer toward a site in which the spiral inclination angle is relatively large from a site in which the spiral inclination angle is relatively small, sufficient pushing performance can be secured using high flexural rigidity of the site in which the spiral inclination angle is relatively large and the tubular body easily pass through a curved site or the like of a biological lumen using the flexible site in which the spiral inclination angle is relatively small. Thus, relatively high reachability and operability can be obtained. Furthermore, the flexural rigidity gradually decreases due to gradual change of the spiral inclination angle of the slit. Therefore, the occurrence of kinking in the medical elongated body without stress concentrated on one place can be reduced even when the tubular body, for example, is rapidly bent.

In accordance with an exemplary embodiment, if the tubular body has a convex portion, which is formed to protrude from one opposed surface of a pair of opposed surfaces constituting the slit, and a concave portion, which is formed such that the convex portion enters the other opposed surface of the opposed surfaces, and the stepped portion is made to be formed in a part of the convex portion or the concave portion, excessive twisting in any rotational direction due to the convex portion entering the concave portion can be suppressed.

In accordance with an exemplary embodiment, if the convex portion is made to be formed to protrude on a side on which the spiral inclination angle of the slit becomes large, out of the distal side or the proximal side, the length sufficient for forming the convex portion in a direction in which the convex portion extends, in a site in which the spiral inclination angle of the slit changes can be secured.

In accordance with an exemplary embodiment, if the width of the convex portion is made to decrease toward the protruding direction, the convex portion can be separated from the concave portion and can return to its original position with respect to the concave portion. Moreover, favorable flexibility can be provided by suppressing the flexural rigidity of the tubular body from locally becoming large.

In accordance with an exemplary embodiment, if the site in which the angle of the slit in the stepped portion changes locally is made to be formed so as to have a curvature, when forming a slit using a laser or the like, the slit can be formed while moving the laser at all times without stopping the laser or the like with respect to a tubular body. For this reason, deterioration or deformation of the material of the tubular body caused by heat, which has been generated by the laser processing and has unnecessarily entered the material of the tubular body can be suppressed. In addition, since the site is formed so as to have a curvature, there is no sharp edge, thereby improving safety.

In the second exemplary embodiment of the medical elongated body which has been constituted as described above, similarly to the first exemplary embodiment, with the provision of a site in which the spiral inclination angles of slits are different from each other, the operability of the medical elongated body can be improved by arbitrarily setting flexibility in accordance with the position in the axial center direction. In addition, a stepped portion and an abutting portion, which abut on each other when the medical elongated body is twisted in a direction in which a spiral is released, are provided in a slit, and therefore, release of a gap of the slit when the medical elongated body is twisted in a direction in which the spiral is released is suppressed. Furthermore, the positions of at least two stepped portions, which are provided in the adjacent slits and are aligned in the axial center direction of the tubular body, are formed to be different in a circumferential direction of the tubular body. Therefore, the stepped portions of the adjacent slits do not overlap each other at the positions in the axial center direction of the tubular body, and it is difficult for the flexural rigidity of the tubular body to be deviated depending on the circumferential direction position. Thus, the tubular body has a favorable flexibility at any position in the circumferential direction. For this reason, the stepped portions and the abutting portions formed in the slits improve the operability due to flexibility of the tubular body while suppressing anisotropy of torque transmission performance in accordance with the rotational direction of the tubular body.

The lengths of the stepped portions in the axial center direction in a site in which the spiral inclination angle of the slit is relatively large are formed longer than those in a site in which the spiral inclination angle of the slit is relatively small. Therefore, it is difficult for the stepped portions to come off from the abutting portions since the lengths of the stepped portions become longer as in a site in which the caught state of a stepped portion with respect to an abutting portion is easily released due to a large spiral inclination angle of the slit. Therefore, the operability can be improved by suppressing anisotropy of torque transmission performance in accordance with the rotational direction.

In accordance with an exemplary embodiment, if the local variation in the angle of the slit in the stepped portion is made to exceed 90 degrees, the stepped portion becomes easily caught by the abutting portion when the medical elongated body is twisted in a direction in which the spiral of the slit is released, and therefore, excessive twisting can be suppressed.

In accordance with an exemplary embodiment, if the range of the inclination angle of the stepped portion with respect to the axial center direction is made to be within ±5 degrees, the stepped portion becomes substantially parallel to the axial center direction, and the stepped portion, which is provided on a side which is convexly curved when the tubular body is curved, that is, a side on which the width of the slit is widened, can move relatively to the abutting portion and becomes easy to return to its original position. For this reason, the flexural rigidity of the tubular body can be suppressed from becoming locally large due to the failure of the movement of the stepped portion to the abutting portion, and therefore, favorable flexibility can be provided.

In accordance with an exemplary embodiment, if the width of the gap of the slit is made to become constant, the shape of a stepped portion, which is formed to protrude from one opposed surface which forms a pair constituting the slit, and the shape of an abutting portion, which is formed on the other opposed surface so as to abut on the stepped portion, become substantially the same as each other. For this reason, a stepped portion becomes easily caught by an abutting portion on an opposed surface when the tubular body is twisted in a direction in which the spiral of the slit is released, and therefore, excessive twisting can be reliably suppressed.

In accordance with an exemplary embodiment, if the tubular body has a site in which the spiral inclination angle gradually changes and the lengths of the plurality of stepped portions which are provided in the site in the axial center direction are made to gradually become longer toward a site in which the spiral inclination angle is relatively large from a site in which the spiral inclination angle is relatively small, sufficient pushing performance can be secured using high flexural rigidity of the site in which the spiral inclination angle of the tubular body is large and to make the tubular body easily pass through a curved site or the like of a biological lumen using the flexible site in which the spiral inclination angle is small. Thus, high reachability and operability can be obtained. Furthermore, the flexural rigidity gradually decreases due to gradual change of the spiral inclination angle of the slit. Therefore, the occurrence of kinking in the medical elongated body can be reduced without stress concentrated on one place even when the tubular body is rapidly bent.

In accordance with an exemplary embodiment, if the tubular body has a convex portion, which is formed to protrude from one opposed surface of a pair of opposed surfaces constituting the slit, and a concave portion, which is formed such that the convex portion enters the other opposed surface of the opposed surfaces, and the stepped portion is made to be formed in a part of the convex portion or the concave portion, excessive twisting in any rotational direction due to the convex portion entering the concave portion can be reduced.

In the third exemplary embodiment of the medical elongated body which has been constituted as described above, similarly to the first and second exemplary embodiments, with the provision of a site in which the spiral inclination angles of slits are different from each other, the operability of the medical elongated body can be improved by arbitrarily setting flexibility in accordance with the position in the axial center direction. In addition, a stepped portion and an abutting portion, which abut on each other when the medical elongated body is twisted in a direction in which a spiral is released, are provided in a slit, and therefore, release of a gap of the slit when the medical elongated body is twisted in a direction in which the spiral is released can be suppressed. Furthermore, since the stepped portion is formed so as to be parallel to the axial center direction, the local variation in the angle of the slit in the stepped portion exceeds 90 degrees and the stepped portion becomes relatively easily caught by the abutting portion. Therefore, excessive twisting can be suppressed. At the same time, the stepped portion, which is provided on a side which is convexly curved when the tubular body is curved, for example, a side on which the width of the slit is widened, can move relatively to the abutting portion and becomes relatively easy to return to its original position. Therefore, the flexural rigidity of the tubular body can be suppressed from becoming locally large due to the failure of the movement of the stepped portion to the abutting portion. For this reason, the stepped portion and the abutting portion formed in the slit improve the operability of the tubular body while suppressing anisotropy of torque transmission performance in accordance with the rotational direction of the tubular body.

In accordance with an exemplary embodiment, the lengths of the stepped portions in a site in which the spiral inclination angle of the slit is relatively large are formed longer than those in a site in which the spiral inclination angle of the slit is relatively small. Therefore, it can be difficult for the stepped portions to come off from abutting portions since the lengths of the stepped portions become longer as in a site in which the caught state of a stepped portion with respect to an abutting portion is easily released due to a large spiral inclination angle of the slit. Therefore, the operability can be improved by suppressing anisotropy of torque transmission performance in accordance with the rotational direction.

In accordance with an exemplary embodiment, if the width of the gap of the slit is made to become constant, the shape of a stepped portion, which is formed to protrude from one opposed surface which forms a pair constituting the slit, and the shape of an abutting portion, which is formed on the other opposed surface so as to abut on the stepped portion, become substantially the same as each other. For this reason, a stepped portion becomes easily caught by an abutting portion on an opposed surface when the tubular body is twisted in a direction in which the spiral of the slit is released, and therefore, excessive twisting can be reliably suppressed.

In accordance with an exemplary embodiment, if the positions of the stepped portions which are provided in the adjacent slits and are aligned in the axial center direction of the tubular body while drawing a spiral, are made to be different in a circumferential direction of the tubular body, the stepped portions of the adjacent slits do not overlap each other in the axial center direction of the tubular body, and it can be difficult for the flexural rigidity of the tubular body to be deviated depending on the circumferential direction position. Therefore, favorable flexibility can be provided.

In accordance with an exemplary embodiment, if the tubular body has a site in which the spiral inclination angle gradually changes and the lengths of the plurality of stepped portions which are provided in the site in the axial center direction are made to gradually become longer toward a site in which the spiral inclination angle is relatively large from a site in which the spiral inclination angle is relatively small, sufficient pushing performance can be secured using high flexural rigidity of the site in which the spiral inclination angle is large and to make the tubular body easily pass through a curved site or the like of a biological lumen using the flexible site in which the spiral inclination angle is small. Thus, high reachability and operability can be obtained. Furthermore, the flexural rigidity gradually decreases due to gradual change of the spiral inclination angle of the slit. Therefore, the occurrence of kinking in the medical elongated body can be reduced without stress concentrated on one place even when the tubular body is rapidly bent.

In accordance with an exemplary embodiment, if the tubular body has a convex portion, which is formed to protrude from one opposed surface of a pair of the opposed surfaces constituting the slit, and a concave portion, which is formed such that the convex portion enters the other opposed surface of the opposed surfaces, and the stepped portion is made to be formed in a part of the convex portion or the concave portion, excessive twisting in any rotational direction can be suppressed due to the convex portion entering the concave portion.

DETAILED DESCRIPTION

Hereinafter, an embodiment of the present invention will be described with reference to the drawings. In some cases, dimensional ratios in the drawings are exaggerated and are different from the actual ratios for the convenience of description.

Figure 1:
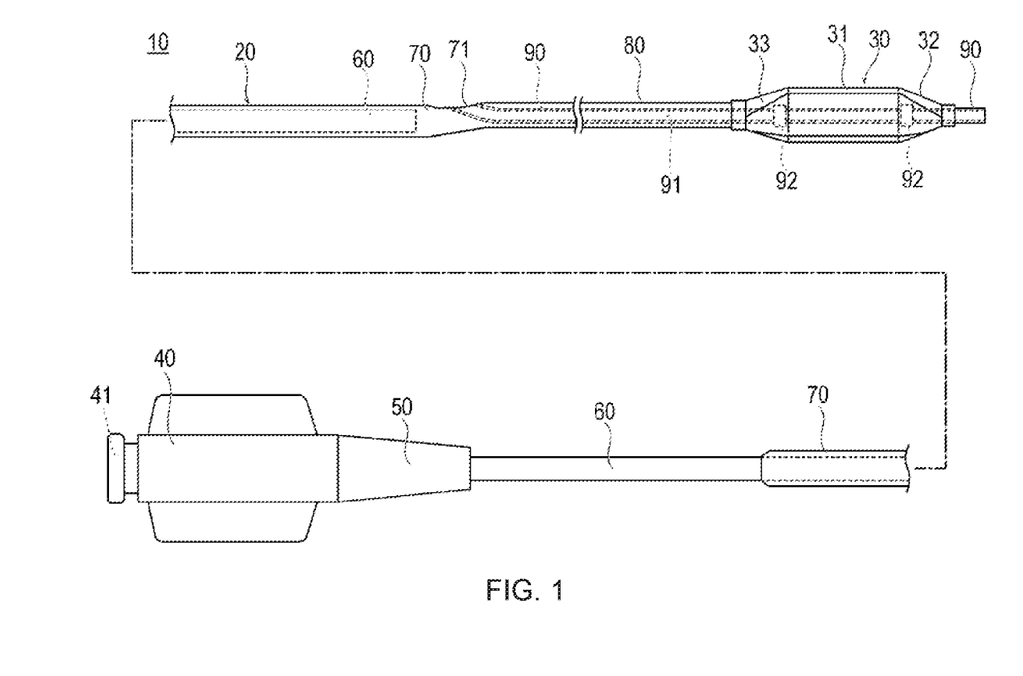
FIG. 1 is a plan view showing a balloon catheter according to an exemplary embodiment of the present disclosure.

A balloon catheter 10 (medical elongated body) according to the present embodiment is a so-called rapid exchange-type catheter and has an elongated catheter main body portion 20, a balloon 30 which is provided at a distal portion of the catheter main body portion 20, a hub 40 which is bonded to a proximal end of the catheter main body portion 20, and an anti-kink tube 50 which is provided in a connection section of between the catheter main body portion 20 and the hub 40. Note that, in the present specification, the side through which the device is inserted into a lumen will be referred to as a "distal end" or a "distal side", and the hand side from which the device is operated will be referred to as a "proximal end" or a "proximal side".

The catheter main body portion 20 can include a tubular proximal shaft 60 (tubular body) of which the distal side is bonded to the hub 40 and which extends in an axial center direction X, a tubular intermediate shaft 70 which covers the distal side of the proximal shaft 60, a tubular distal shaft 80 which is provided on the distal side of the intermediate shaft 70, and a tubular inner tube shaft 90 which is disposed inside the distal shaft 80. An expansion lumen through which an expansion fluid for expanding the balloon 30 flows is formed inside the proximal shaft 60, the intermediate shaft 70, and the distal shaft 80.

Figure 2:
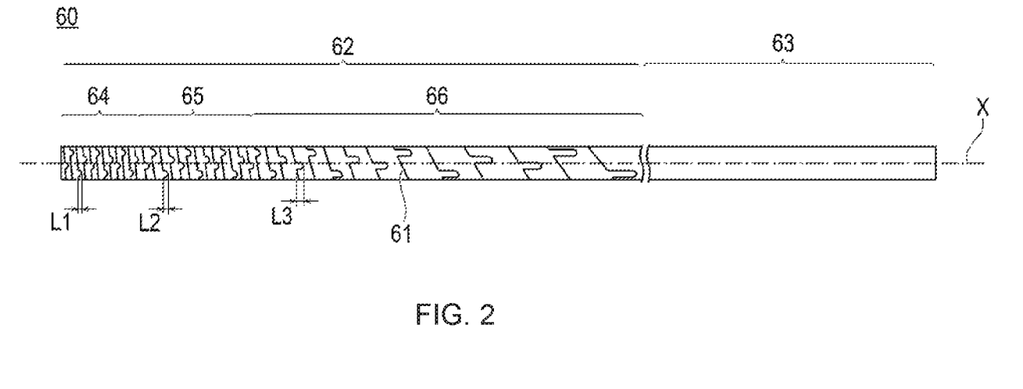
FIG. 2 is a plan view showing a proximal shaft.

The proximal shaft 60 can include a flexible portion 62 on a distal side on which a spiral slit 61 is formed, and a high rigidity portion 63 on a proximal side on which the slit 61 is not formed. The flexible portion 62 can include a first flexible portion 64 on the most distal side, a second flexible portion 65 which is provided on a proximal side of the first flexible portion 64, and a third flexible portion 66 which is provided on a proximal side of the second flexible portion 65. The site including the flexible portion 62 on the distal side of the proximal shaft 60 is disposed inside the intermediate shaft 70 and extends to the vicinity of a guide wire port 71, which is provided in the intermediate shaft 70. The slit 61 is formed through spiral slit processing using a technique, for example, laser processing, which is generally performed.

A slit 61 is formed at a predetermined pitch on the first flexible portion 64 and is formed at a predetermined pitch which is wider than on the first flexible portion 64 on the second flexible portion 65. The third flexible portion 66 is formed such that the pitch of the slit 61 gradually becomes wider toward the proximal side from the second flexible portion 65 side. Note that the slit 61 formed on the first flexible portion 64, the second flexible portion 65, and the third flexible portion 66 can be formed as one continuous slit 61. Here, the pitch refers to a gap between two adjacent slits, which are formed on the tubular body.

The spiral inclination angle α which is an angle in an extending direction of a spiral of the slit 61 with respect to a cross-section orthogonal to the axial center direction X differs in the first flexible portion 64, the second flexible portion 65, and the third flexible portion 66. In general, the spiral inclination angle α becomes smaller as the pitch of the slit 61 is narrower and becomes larger as the pitch of the slit 61 is wider.

In accordance with an exemplary embodiment, with the formation of the slit 61, the flexible portion 62 of the proximal shaft 60 has a flexible structure in which the flexible portion is easily bent due to decreased flexural rigidity of the flexible portion. The pitch of the slit 61 of the first flexible portion 64 is narrowest, and therefore, the flexural rigidity of the first flexible portion is lower than those of the second flexible portion 65 and the third flexible portion 66. The pitch of the slit 61 of the second flexible portion 65 is wider than that of the first flexible portion 64 and the pitch of the slit 61 of the second flexible portion is narrower than that of the third flexible portion 66. Therefore, the flexural rigidity of the second flexible portion is higher than that of the first flexible portion 64 and is lower than that of the third flexible portion 66. The pitch of the slit 61 of the third flexible portion 66 can be designed to gradually become narrower toward the distal side, and therefore, the flexural rigidity becomes lower toward the distal side. In this manner, the proximal shaft 60 has sufficient rigidity on the proximal side and has a flexible structure toward the distal side. Therefore, sufficient pushing performance of the balloon catheter 10 can be secured using the site on the proximal side on which the flexural rigidity is high, and the balloon catheter 10 can easily pass through a curved site of a biological lumen using the flexible site on the distal side on which the flexural rigidity is low. Thus, high reachability and operability can be obtained. In addition, the pitch of the slit 61 changes stepwise and the flexural rigidity in the third flexible portion 66 decreases gradually (gradiently) toward the distal side. Therefore, the occurrence of kinking in the catheter main body portion 20 can be reduced without stress being concentrated on one place even when the proximal shaft 60 is rapidly bent.

Figure 3:
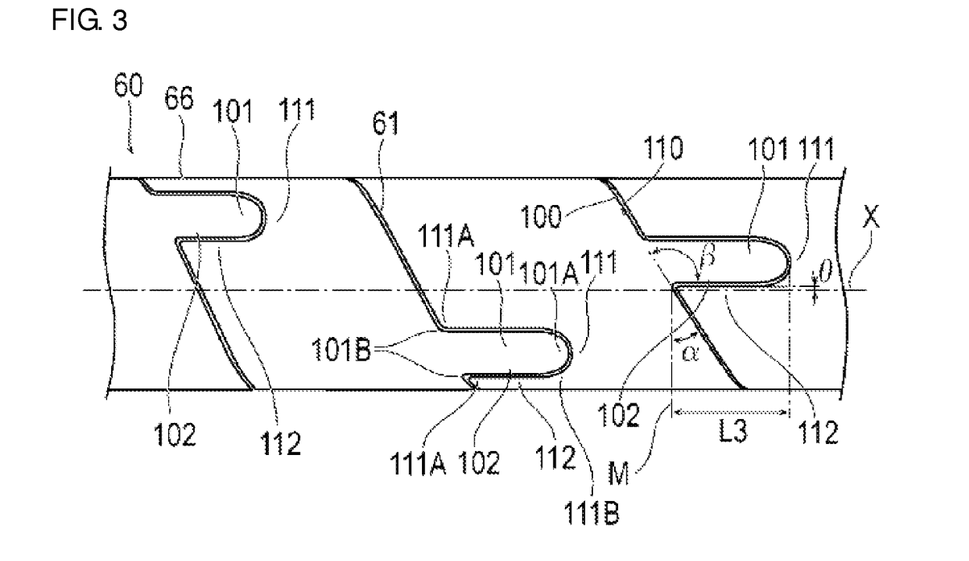
FIG. 3 is a plan view in which a part of the proximal shaft is enlarged.
Figure 4:
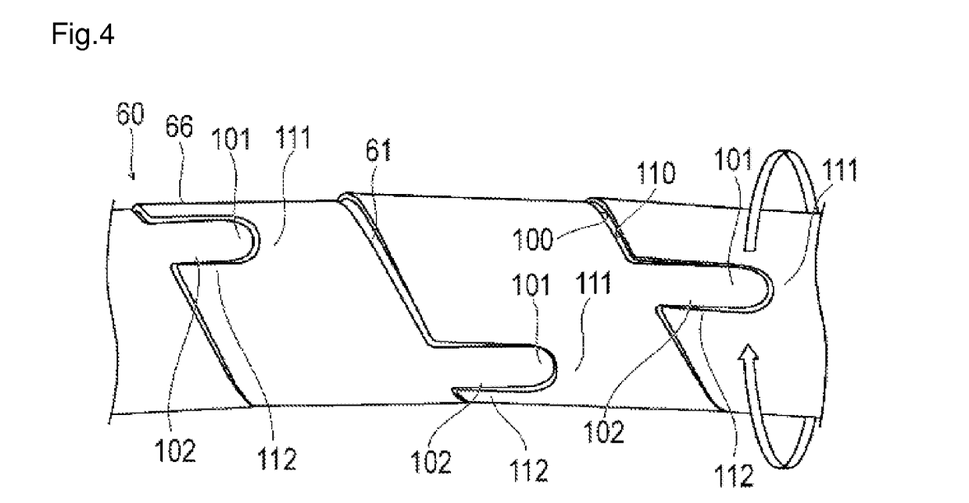
FIG. 4 is a plan view in which a part of the proximal shaft is enlarged when torque has acted on the balloon catheter.
Figure 5:
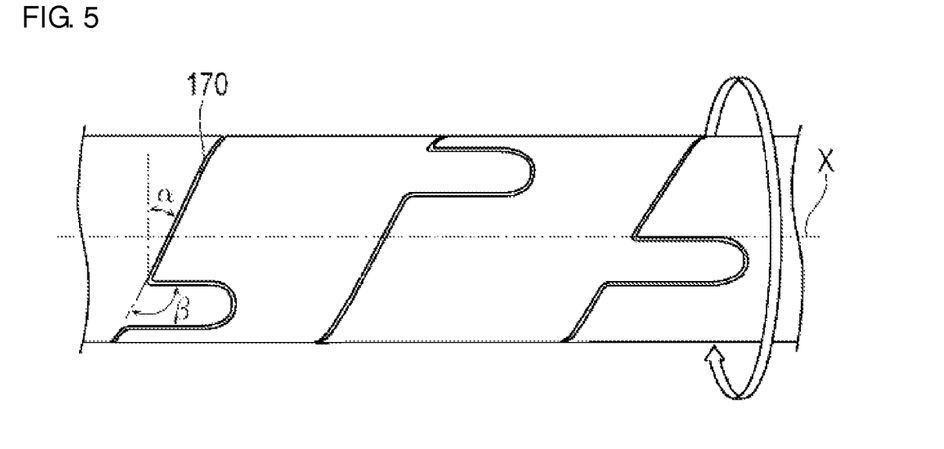
FIG. 5 is a plan view showing a modification example of the proximal shaft when torque has acted on the balloon catheter.

The slit 61 is constituted of a pair of opposed surfaces 100 and 110 which are disposed opposite to each other. A plurality of convex portions 101, which are formed to protrude are formed on one opposed surface 100 of the opposed surfaces and a plurality of concave portions 111 into which the convex portions 101 enter are formed on the other opposed surface 110 of the opposed surfaces. The convex portion 101 has a stepped portion 102 in which the angle of the slit 61 changes locally with respect to the spiral inclination angle α and which is formed stepwise. As shown in FIG. 4, when proximal shaft 60 is twisted in a direction (refer to a void arrow in a case where the device is operated from the arrow side in FIG. 4) in which the spiral of the slit 61 is released, the stepped portion 102 plays a role of abutting on an abutting portion 112 which is disposed so as to be opposed to the stepped portion 102 and suppressing excessive twisting. In accordance with an exemplary embodiment, the stepped portion 102 is a portion in which the angle of the slit 61 changes locally with respect to the spiral inclination angle α which is formed in the convex portion 101, and is a portion which abuts on the concave portion 111 when the proximal shaft 60 (tubular body) having the slit 61 is twisted in a direction in which the spiral is released. In addition, a slit 170 in a direction reverse to the direction of the slit in FIG. 4 may be formed as shown in FIG. 5. In this case, the direction in which the spiral of the slit 170 is released becomes a direction reverse to the direction of the slit in FIG. 4.

Figure 8:
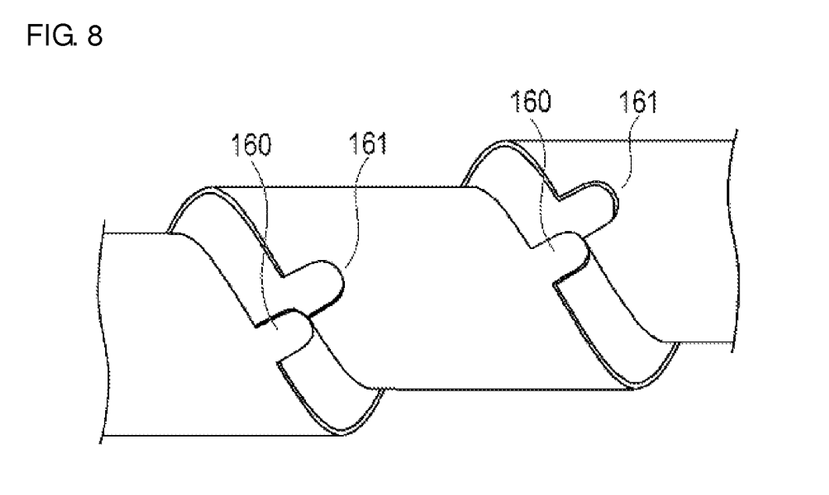
FIG. 8 is a plan view showing a comparative example of the proximal shaft.

As shown in FIGS. 2 and 3, lengths L1 to L3 of stepped portions 102 in the axial center direction X in a site in which the pitch of the slit 61 is relatively large can be formed to be longer than those in a site in which the pitch thereof is relatively small. Accordingly, the length L2 of the stepped portion 102 which is provided in the second flexible portion 65 in which the pitch of the slit 61 is wider than that of the first flexible portion 64 is longer than the length L1 of a stepped portion 102 which is formed in the first flexible portion 64. In addition, the length L3 of a stepped portion 102 which is provided in the third flexible portion 66 in which the pitch of the slit 61 is wider than that of the second flexible portion 65 is longer than the length L2 of the stepped portion 102 which is formed in the second flexible portion 65. Moreover, the length L3 of the stepped portion 102 which is provided in the third flexible portion 66 in which the pitch gradually becomes wider toward the proximal direction becomes longer toward the stepped portion 102 on the proximal side. In accordance with an exemplary embodiment, for example, the lengths L1 to L3 of the stepped portions 102 become longer toward a stepped portion 102 which is provided in a site in which the pitch becomes wider and the spiral inclination angle α becomes larger. As shown in a comparative example in FIG. 8, a convex portion 160 is completely detached from a concave portion 161 as in a site in which the pitch becomes wider, the spiral inclination angle α becomes larger, and it can be difficult for the convex portion to return to its original position. In contrast, in the present exemplary embodiment, the convex portion 101 can be made to be hardly detached from the concave portion 111 in accordance with the degree of the spiral inclination angle α by making the lengths L1 to L3 of the stepped portions 102 larger as a stepped portion 102 is provided in a site in which the spiral inclination angle α becomes larger. Here, the length of the stepped portion 102 in the axial center direction X refers to a distance between a straight line orthogonal to the axial center direction X which comes into contact with the convex portion 101 and a straight line orthogonal to the axial center direction X which passes through a site in which the slit angle changes locally on the opposed surface 100 of the slit 61 having a spiral inclination angle α.

In addition, in the distal portion in a protruding direction, the width of the convex portion 101 decreases toward the protruding direction. For this reason, the convex portion 101 can move in a direction, in which the convex portion is detached from the concave portion 111, and can return to its original position with respect to the concave portion 111. Moreover, favorable flexibility can be provided by suppressing the flexural rigidity of the proximal shaft 60 from locally becoming large.

In addition, in the stepped portion 102, the local variation $\beta$ in the angle of the slit 61 preferably exceeds 90 degrees. In accordance with an exemplary embodiment, for example, it can be preferable that the angle which is formed by the stepped portion 102 of the convex portion 101 is formed so as to exceed 90 degrees with respect to the opposed surface 100 of the slit 61 having a spiral inclination angle α. With such a configuration, when the proximal shaft 60 is twisted in a direction in which the spiral of the slit 61 is released, the stepped portion 102 which is provided in the convex portion 111 becomes easily caught by the abutting portion 112 which is provided in the concave portion 111 as shown in FIG. 4, and therefore, excessive twisting can be reliably suppressed. In addition, when the proximal shaft 60 is twisted in a direction in which the spiral is released, the convex portion 101 can be suppressed from being detached from the concave portion 102. At this time, in order to more reliably exhibit the above-described effect, it can be preferable, for example, that the angle which is formed by the abutting portion 112 of the convex portion 101 is formed so as not to exceed 90 degrees with respect to the opposed surface 110 of the slit 61 having a spiral inclination angle α. Note that the local variation β in the angle of the slit 61 may not exceed 90 degrees.

In addition, it can be, for example, more preferable that the stepped portion 102 is formed so as to be substantially parallel to the axial center direction X and that the range of an inclination angle θ with respect to the axial center direction X is at least within, for example, ±5 degrees. With the stepped portion 102 which is formed to be substantially parallel to the axial center direction X within, for example, ±5 degrees, the convex portion 101, which is provided on a side which is convexly curved when the proximal shaft 60 is curved, for example, a side on which the width of the gap of slit 61 is widened, can be easily separated from the concave portion 111 while moving the inside of the concave portion and becomes easy to return to its original position with respect to the concave portion 111. For this reason, the flexural rigidity of the proximal shaft 60 can be suppressed from becoming locally large due to the failure of the separation of the convex portion 101 from the concave portion 111, and therefore, favorable flexibility can be provided. In addition, it can be more preferable, for example, that the stepped portion 102 is formed so as to be parallel to the axial center direction X in that the convex portion 101 which is provided on the side on which the width of the gap of the slit 61 is widened is easily separated from the concave portion 111 while moving the inside of the concave portion. Note that the range of the inclination angle θ of the stepped portion 102 with respect to the axial center direction X may not be within, for example, ±5 degrees.

In addition, it can be preferable that the width of the gap of slit 61 is formed to be constant, for example, the width between the opposed surfaces 100 and 110 of the slits is constant. With such a configuration, the shapes of outlines of the convex portion 101 and the concave portion 111 become substantially the same as each other. For this reason, when the proximal shaft 60 is twisted in a direction in which the spirals of the slits 61 are released, the stepped portion 102 provided in the convex portion 101 becomes easily caught by the abutting portion 112 which is provided in the concave portion 111 as shown in FIG. 4, and therefore, excessive twisting can be reliably suppressed. In addition, when the proximal shaft 60 is twisted in a direction in which the spirals are released, the convex portion 101 can be suppressed from being detached from the concave portion 111.

In addition, the positions of stepped portions 102, which are provided in adjacent slits 61 and are aligned in the axial center direction X while drawing a spiral, are different in a circumferential direction of the proximal shaft 60, and therefore, adjacent stepped portions 102 do not overlap each other in the axial center direction X. In accordance with an exemplary embodiment, for example, at least two continuous adjacent stepped portions 102 do not overlap each other in the axial center direction X. For example, the stepped portions 102 can be formed at, for example, 125 degrees, 270 degrees, or 450 degrees in the circumferential direction of the proximal shaft 60 along the spiral. Accordingly, favorable flexibility can be provided without deviation of the flexural rigidity of the proximal shaft 60 depending on the circumferential direction position. Note that the stepped portions 102 may not be formed at the same angles as each other in the circumferential direction of the proximal shaft 60. In addition, all of the stepped portions 102 may not overlap each other at all in the axial center direction of the proximal shaft 60.

In addition, the convex portion 101 is formed to protrude on the proximal side which is a side on which the spiral inclination angle α of a slit 61 becomes large, for example, a side on which the pitch of the slit is widened, out of the distal side or the proximal side. For this reason, the length sufficient for forming the convex portion 101 can be secured in a direction in which the convex portion 101 extends, in a site in which the pitch of the slit 61 changes. Note that the convex portion may be formed to protrude in a direction in which the pitch of the slit becomes narrower, out of the distal side or the proximal side. In addition, the direction of convex portions may vary depending on each of the convex portions.

Sites in which the angle of a slit 61 changes locally, for example, a corner portion 101A which becomes a convex shape of an edge of the convex portion 101, a corner portion 101B which becomes a concave shape of an edge of the convex portion 101, a corner portion 111A which becomes a convex shape of an edge of the concave portion 111, and a corner portion 111B which becomes a concave shape of an edge of the concave portion 111 can be formed so as to have a curvature. For this reason, when forming a slit 61 using a laser or the like, it is unnecessary to stop the laser or the like, which is used for processing the aforementioned corner portions 101A and 111A and corner portions 101B and 111B, with respect to a tubular body which becomes a material. Therefore, the slit 61 can be formed while moving the laser or the like with respect to the tubular body at all times. For this reason, heat generated through the laser processing performed on the corner portions 101A and 111A and corner portions 101B and 111B does not unnecessarily come in, and therefore, the occurrence of deterioration or deformation in the material of the tubular body can be suppressed. In addition, since the corner portions 101A and 111A and corner portions 101B and 111B are formed with a curvature, there is no sharp edge, thereby improving safety.

Metals, for example, Ni—Ti, brass, SUS, aluminum and the like, which have comparatively high rigidity are preferably used for the proximal shaft 60. Note that resins, for example, polyimide, vinyl chloride, and polycarbonate can be used, as long as they have comparatively high rigidity.

The dimension of the high rigidity portion 63 of the proximal shaft 60 is not particularly limited, but the high rigidity portion is a tubular body of which the outer diameter can be, for example, about 0.5 mm to 3.5 mm, the thickness can be, for example, about 10 μm to 170 μm, and the length can be, for example, about 1100 mm to 1400 mm.

The dimension of the first flexible portion 64 of the proximal shaft 60 is not particularly limited, but the first flexible portion can have an outer diameter of, for example, about 0.5 mm to 3.5 mm, a thickness of, for example, about 10 μm to 170 μm, and a pitch of, for example, about 0.1 mm to 0.5 mm.

The dimension of the second flexible portion 65 of the proximal shaft 60 is not particularly limited, but the second flexible portion can have an outer diameter of, for example, about 0.5 mm to 3.5 mm, a thickness of, for example, about 10 μm to 170 μm, and a pitch of, for example, about 0.5 mm to 1.5 mm.

The dimension of the third flexible portion 66 of the proximal shaft 60 is not particularly limited, but the third flexible portion can have an outer diameter of, for example, about 0.5 mm to 3.5 mm, a thickness of, for example, about 10 μm to 170 μm, and a pitch of, for example, about 1.5 mm to 5.0 mm.

The width of the gap of the slit 61 is not particularly limited, but can be, for example, about 0.01 mm to 0.05 mm.

The material constituting the distal shaft 80, the inner tube shaft 90, and the intermediate shaft 70 is not particularly limited, and examples thereof include polymer materials, for example, polyolefins (for example, polyethylene, polypropylene, polybutene, ethylene-propylene copolymer, ethylene-vinyl acetate copolymer, ionomer, a mixture of two or more thereof), crosslinked bodies of polyolefin, polyvinyl chloride, polyamide, polyamide elastomer, polyester, polyester elastomer, polyurethane, polyurethane elastomer, fluororesin, and polyimide, and a mixture thereof.

The distal shaft 80 and the intermediate shaft 70 are not particularly limited, but is a tubular body of which the outer diameter can be, for example, 0.7 mm to 1.7 mm and the thickness can be, for example, 25 μm to 250 μm. The length of the intermediate shaft 70 is not particularly limited, but can be, for example, about 100 mm to 150 mm. The length of the distal shaft 80 is not particularly limited, but can be, for example, 230 mm to 250 mm.

As shown in FIG. 1, the inner tube shaft 90 coaxially penetrates the inside of the distal shaft 80 and the balloon 30. The distal portion of the inner tube shaft 90 is extended from the distal end of the balloon 30 and is connected to the distal side of the balloon 30 in a state where liquid-tightness therebetween is maintained. In contrast, the proximal end of the inner tube shaft 90 is bonded to a part (side port which is formed on a side surface) in the outer circumferential direction of the intermediate shaft 70 in a state where liquid-tightness therebetween is maintained. A proximal aperture of the inner tube shaft 90 is exposed to the outside of the intermediate shaft 70 to constitute the guide wire port 71. The internal space from the distal end of the inner tube shaft 90 to the guide wire port 71 is made to be a guide wire lumen 91. The guide wire is inserted into the inner tube shaft 90 having a distal aperture of the inner tube shaft 90 as an inlet and having a guide wire port 71 as an outlet. Note that the guide wire port 71 may not be provided in the intermediate shaft 70, but may be provided in the proximal shaft 60 or the distal shaft 80, or may be provided in a boundary region (connection region) between the intermediate shaft 70 and the distal shaft 80.

A radiopaque marker 92 can be provided around the inner tube shaft 90 of the inside of the balloon 30 so as to be able to form an image using an X-ray. The radiopaque marker 92 is preferably formed of a coil spring or a ring, and one or more thereof can be provided. It is preferable to use a material having a high capability of forming an X-ray image, for example, Pt, Pt alloy, W, W alloy, Au, Au alloy, Ir, Ir alloy, Ag, and Ag alloy, as the material of the radiopaque marker 92.

The hub 40 can include a proximal aperture 41 functioning as a port which communicates with the expansion lumen of the catheter main body portion 20 and through which an expansion fluid is made to flow in and out. The hub is fixed to the proximal shaft 60 in a state where liquid-tightness therebetween is maintained.

Examples of the constituent material of the hub 40 which can be favorably used include thermoplastic resins, for example, ABS resin, polycarbonate, polyamide, polysulfone, polyarylate, and methacrylate-butylene-styrene copolymers. In addition, these materials may be arbitrarily combined with each other.

The anti-kink tube 50 is placed outside the proximal shaft 60 in order to prevent kinking (bending) of the proximal shaft 60 in the vicinity of the distal end of the hub 40.

The balloon 30 widens a stenosed site by being expanded, or expands a stent in a case where the stent is disposed in the outer circumference of the balloon 30. The balloon has a cylindrical portion 31 which has a substantially constant diameter and is formed in a central portion in the axial direction in a substantially cylindrical shape so as to efficiently expand a predetermined range. A first decreased diameter portion 32 which is formed in a tapered shape and of which the diameter decreases toward the distal side, is provided on the distal side of the cylindrical portion 31 of the balloon 30. A second decreased diameter portion 33 which is formed in a tapered shape and of which the diameter decreases toward the proximal side is provided on the proximal side of the cylindrical portion of the balloon.

The distal side of the first decreased diameter portion 32 is connected to the outer wall surface of the inner tube shaft 90 in a state where liquid-tightness therebetween is maintained. The proximal side of the second decreased diameter portion 33 is connected to the outer wall surface of the distal portion of the distal shaft 80 in a state where liquid-tightness therebetween is maintained. Accordingly, the inside of the balloon 30 communicates with the expansion lumen, which is formed in the catheter main body portion 20, and is designed such that an expansion fluid can flow in from the proximal side through the expansion lumen. The balloon 30 is expanded by the inflow of the expansion fluid and enters a state of being folded through discharging the expansion fluid, which has flowed in.

The expansion fluid may be a gas or a liquid, and examples thereof include gases, for example, air, helium gas, $CO_2$ gas, $O_2$ gas and the like, or liquids, for example, a physiological salt solution, a contrast agent and the like.

The balloon 30 is preferably formed of a material having flexibility to some degree, and examples of such a material include polyolefins, for example, polyethylene, polypropylene, polybutene, ethylene-propylene copolymers, ethylene-vinyl acetate copolymers, ionomer, and a mixture of two or more thereof; thermoplastic resins, for example, a soft polyvinyl chloride resin, polyamide, polyamide elastomer, polyester, polyester elastomer, polyurethane, fluororesin and the like; and silicone rubber, and latex rubber.

The dimension of the balloon 30 is not particularly limited, but the outer diameter of the cylindrical portion 31 when the balloon is expanded can be, for example, 1.0 mm to 15.0 mm, the length thereof can be, for example, 5 mm to 50 mm, and the whole length of the balloon can be, for example, 10 mm to 90 mm.

Next, a case of inserting the balloon catheter 10 into a blood vessel for use will be described as an example of a method of using the balloon catheter according to the present exemplary embodiment.

First, air in the balloon 30 and the expansion lumen is drawn out as much as before treating a stenosed site of a blood vessel, and the inside of the balloon 30 and the expansion lumen is replaced with an expansion fluid. At this time, the balloon 30 enters a state of being folded.

Next, a sheath is indwelled in the blood vessel of a patient through, for example, the Seldinger technique, and a guide wire and the balloon catheter 10 are inserted into the blood vessel through the inside of the sheath in a state where the guide wire has been inserted through the inside of the guide wire lumen 91. Subsequently, the balloon catheter 10 is made to proceed while the guide wire is advanced, and the balloon 30 is made to reach the stenosed site.

Next, a predetermined amount of an expansion fluid is injected through a proximal aperture 41 of the hub 40 using an indeflator, a syringe, or pump, in a state where the balloon 30 is positioned at the stenosed site and the expansion fluid is sent to the inside of the balloon 30 through the expansion lumen to expand the folded balloon 30. Accordingly, the cylindrical portion 31 of the balloon 30 can widen the stenosed site. In addition, when using a stent delivery system in which a stent is disposed in the outer circumference of the balloon 30, the stent delivery system can be favorably maintained in a state where the stent is widened while the stent is plastically deformed and the stenosed site is expanded by the stent.

Thereafter, the expansion fluid is discharged by being aspirated by the proximal aperture 41, and the device enters a state where the balloon 30 is contracted and folded. Note that, in a case where the stent is used as the stent delivery system, the stent is indwelled in the stenosed site while a state where the stent is expanded is maintained. Then, the guide wire and the catheter main body portion 20 are removed from the blood vessel through the sheath, and the procedure is completed.

As described above, with the provision of the site in which spiral inclination angles α of the slit 61 are different from each other, the operability of the balloon catheter 10 can be improved according to the present embodiment by arbitrarily setting flexibility in accordance with the position in the axial center direction X. Since the stepped portion 102 in which the angle of the slit 61 with respect to a spiral inclination angle α changes locally is formed on one opposed surface 100 of the a pair of opposed surfaces 100 and 110 constituting the slit, and the abutting portion 112 on which the stepped portion 102 abuts when the proximal shaft 60 is twisted in a direction in which the spiral of the slit 61 is released is formed on the other opposed surface 110 of the opposed surfaces. Therefore, the stepped portion 102 abuts on the abutting portion 112 when the proximal shaft is twisted in a direction in which the spiral is released, and generation of a gap of slit 61 is suppressed. Furthermore, the lengths L1 to L3 of the stepped portions 102 in the axial center direction X in a site in which the spiral inclination angle α of the slit 61 is relatively large are formed to be longer than those in a site in which the spiral inclination angle thereof is relatively small. Therefore, it can be difficult for the stepped portions 102 to come off from the abutting portions 112 since the lengths of the stepped portions becomes longer as in a site in which the caught state of the stepped portion 102 with respect to the abutting portion 112 is easily released due to a large inclination angle of the slit 61. Therefore, the operability can be improved by suppressing anisotropy of torque transmission performance in accordance with the rotational direction.

In addition, the release of the slits can be suppressed by making the states of the slits separated into pieces so as to, for example, partially connect the opposed surfaces to each other which constitute the slits. However, in this case, stress is concentrated on a site on which the opposed surfaces are connected to each other. Therefore, deformation, fracture, or an unexpected operation can be caused by the material, which has been fatigued. In contrast, in the present embodiment, the slit 61 is formed continuously without being disconnected. Therefore, deformation, fracture, or an unexpected operation caused by the material, which has been fatigued, can be suppressed.

In addition, the local variation β in the angle of the slit 61 with respect to the spiral inclination angle α exceeds 90 degrees. Therefore, the stepped portion 102 becomes easily caught by the abutting portion 112 when the proximal shaft 60 is twisted in a direction in which the spiral of the slit 61 is released, and therefore, excessive twisting can be reliably suppressed.

In addition, since the range of the inclination angle θ of the stepped portion 102 with respect to the axial center direction X is within, for example, ±5 degrees, the stepped portion 102 becomes substantially parallel to the axial center direction X, and the stepped portion 102, which is provided on a side which is convexly curved when the proximal shaft 60 is curved, for example, a side on which it is necessary to widen the width of the slit 61, can move in the concave portion 111 and becomes easy to return to its original position with respect to the concave portion 111. For this reason, the flexural rigidity of the proximal shaft 60 can be suppressed from becoming locally large due to the failure of the movement of the convex portion 101 from the concave portion 111, and therefore, favorable flexibility can be provided.

In addition, the width of the gap of slit 61 becomes constant. Therefore, the shape of a stepped portion 102, which is formed to protrude from one opposed surface 100 of a pair of opposed surfaces 100 and 110 constituting the slit 61, and the shape of an abutting portion 112, which is formed on the other opposed surface 110 so as to abut on the stepped portion 102, become substantially the same as each other. For this reason, the shapes of the outline of the convex portion 101, which is formed to protrude from one opposed surface of a pair of opposed surfaces 100 and 110 constituting the slit 61, and the outline of the concave portion 111, which is formed such that the convex portion 101 enters the other opposed surface of the opposed surfaces 100 and 110, become substantially the same as each other. For this reason, the stepped portion 102 which is provided in the convex portion 101 becomes easily caught by the abutting portion 112 which is provided in the concave portion 111 when the proximal shaft 60 (tubular body) is twisted in a direction in which the spiral of the slit 61 is released, and therefore, excessive twisting can be reliably suppressed.

In addition, the positions of stepped portions 102, which are provided in adjacent slits 61 and are aligned in the axial center direction X of the proximal shaft 60 (tubular body) while drawing a spiral, are different in a circumferential direction of the proximal shaft 60, and therefore, the stepped portions 102 do not overlap each other in the axial center direction X of the proximal shaft 60. For this reason, favorable flexibility can be provided without deviation of the flexural rigidity of the proximal shaft 60 depending on the circumferential direction position.

In addition, the proximal shaft 60 (tubular body) has a site in which the spiral inclination angle α gradually changes and the lengths L3 of a plurality of stepped portions 102 which are provided in the site in the axial center direction X gradually become longer toward a site in which the spiral inclination angle α is relatively large from a site in which the spiral inclination angle is relatively small. Therefore, sufficient pushing performance can be secured using high rigidity of the site in which the spiral inclination angle α of the proximal shaft 60 is large and the proximal shaft can easily pass through a curved site or the like of a biological lumen using high flexibility of the site in which the spiral inclination angle α is small. Thus, high reachability and operability can be obtained. Furthermore, the flexural rigidity gradually decreases due to gradual change of the spiral inclination angle α. Therefore, the occurrence of kinking in the balloon catheter 10 can be reduced without stress concentrated on one place even when the proximal shaft 60 is rapidly bent.

In addition, the proximal shaft 60 (tubular body) has the convex portion 101, which is formed to protrude from one opposed surface 100 constituting the slit 61, and the concave portion 111, which is formed such that the convex portion 101 enters the other opposed surface 110, and the stepped portion 102 is formed in a part of the convex portion 101 or the concave portion 111. Therefore, excessive twisting can be suppressed even in any rotational direction due to the convex portion 101 entering the concave portion 111.

In addition, the convex portion 101 can be formed to protrude on a side (proximal side in the present embodiment) which is in a direction in which the spiral inclination angle α becomes large, out of the distal side or the proximal side. Therefore, the length sufficient for forming the convex portion 101 in a direction in which the convex portion 101 extends can be secured, in a site in which the spiral inclination angle α changes.

In addition, since the width of the convex portion 101 decreases toward the protruding direction, the convex portion 101 can be separated from the concave portion 111 and can return to its original position with respect to the concave portion 111. Moreover, favorable flexibility can be provided by suppressing the flexural rigidity of the proximal shaft 60 from locally becoming large.

In addition, the site in which the angle of the slit 61 in the stepped portion 102 changes locally is formed so as to have a curvature. Therefore, when forming a slit 61 using a laser or the like, the slit can be formed while moving the laser or the like at all times without stopping the laser or the like with respect to a tubular body. For this reason, deterioration or deformation of the material of the tubular body caused by heat, which has been generated by the laser processing and has unnecessarily entered the material of the tubular body can be suppressed. In addition, since the site is formed so as to have a curvature, there is no sharp edge, thereby improving safety.

Note that the present disclosure is not limited only to the above-described embodiment, and various modifications can be made by those skilled in the art within technical ideas of the present disclosure. For example, in the present embodiment, the stepped portion 102 is formed in the convex portion 101 and the abutting portion 112 is formed in the concave portion 111. However, a stepped portion may be formed in a concave portion and an abutting portion can be formed in a convex portion depending on the conditions, for example, the direction in which the convex portion protrudes or the like.

Figure 6:
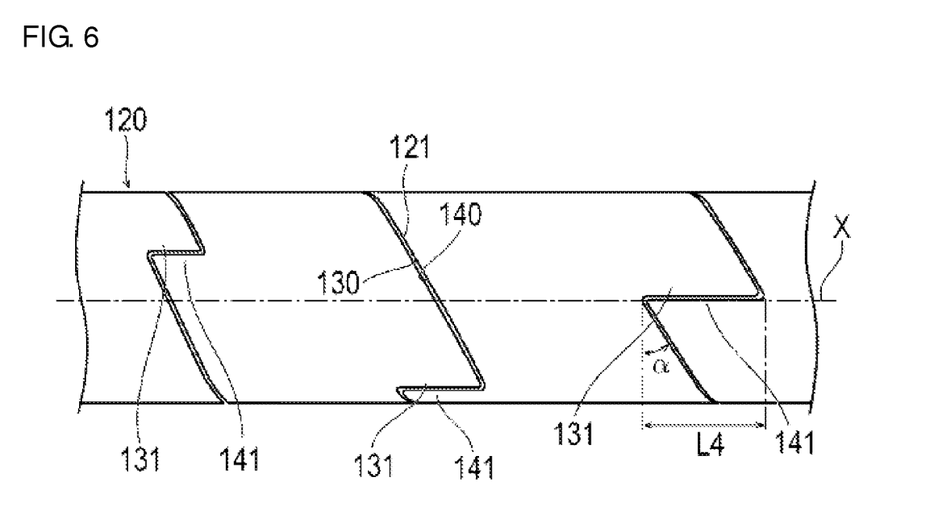
FIG. 6 is a plan view showing a modification example of the proximal shaft.

In addition, a stepped portion 131 and an abutting portion 141 on which the stepped portion 131 abuts may be formed without forming any convex portion and concave portion in a slit 121 of a proximal shaft 120 (tubular body) as in a modification example shown in FIG. 6. In accordance with an exemplary embodiment, for example, the stepped portion 131 in which the angle of the slit 121 of the proximal shaft 120 with respect to a spiral inclination angle α changes locally is formed on one opposed surface 130 of a pair of opposed surfaces 130 and 140 constituting the slit, and the abutting portion 141 on which the stepped portion 131 abuts when the proximal shaft 120 is twisted in a direction in which the spiral of the slit 121 is released is formed on the other opposed surface 140 of the opposed surfaces. Then, the lengths L4 of stepped portions 131 in an axial center direction X in a site in which the spiral inclination angle α is relatively large are formed to be longer than those in a site in which the spiral inclination angle is relatively small. Even with such a structure, a stepped portion 131 abuts on the abutting portion 141 when the proximal shaft 120 is twisted in a direction in which the spiral of the slit is released, and therefore, release of a gap of slit 121 is suppressed. Moreover, the operability can be improved by suppressing anisotropy of torque transmission performance in accordance with the rotational direction, using the stepped portion 131 which the lengths L4 in a site in which the spiral inclination angle α of the slit 121 is relatively large is longer than that in a site in which the spiral inclination angle of the slit is relatively small.

Figure 7:
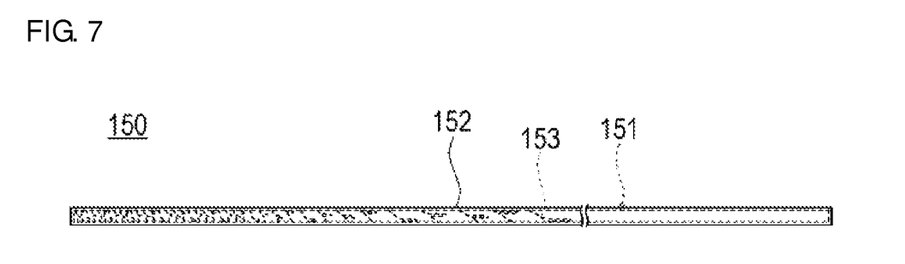
FIG. 7 is a plan view showing a case where a tubular body is applied to a guide wire.

In addition, the medical elongated body according to the present embodiment is the balloon catheter 10. However, the disclosure is not particularly limited as long as the medical elongated body is an elongated body for a medical purpose, and the medical elongated body may be catheters for other purposes, for example, a micro catheter, an imaging catheter or the like, or a guide wire 150 or the like as shown in FIG. 7. The guide wire 150 can include a tubular body 151, on which a spiral slit 153 is formed, and a coated layer 152 which is formed of a polymer or the like with which the tubular body 151 is coated. Note that the configuration of the guide wire is not particularly limited as long as the guide wire can include a tubular body.

In addition, in the medical elongated body according to the present embodiment, the proximal shaft 60 (tubular body) can include three flexible portions including the first flexible portion 64, the second flexible portion 65, and the third flexible portion 66, of which the spiral inclination angles α of the slit 61 are different from each other. However, the configuration of the disclosure is not limited as long as there are sites of which the spiral inclination angles α are different from each other. For example, there may be no site, such as the third flexible portion 66, in which the spiral inclination angle α of the slit 61 gradually changes, or only the site, such as the third flexible portion 66, in which the spiral inclination angle α of the slit 61 gradually changes, may be formed. In addition, in the medical elongated body according to the present embodiment, the spiral inclination angle α of the slit 61 becomes smaller toward the distal side. However, the positional relationship between sites in which the spiral inclination angles α of the slit are different from each other is not particularly limited. For example, the spiral inclination angle α may become large toward the distal side, or a site in which the spiral inclination angle α is large and a site in which the spiral inclination angle α is small may be alternately disposed. In addition, the direction of the spiral of the slit is not limited. Alternately, the disclosure may have a multiple spiral structure having a plurality of slits. In addition, slits may be provided over the entire shaft, which may be covered with a polymer tube.

The detailed description above describes a medical elongated body, which is inserted into a biological lumen, for example, a blood vessel. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body, the medical elongated body comprising:
 a tubular body, which extends in an axial center direction, at least a part of the tubular body having a spiral slit, the tubular body including sites in which spiral inclination angles of the spiral slit in an extending direction of a spiral of the spiral slit with respect to a cross-section orthogonal to the axial center direction are different from each other, and a stepped portion in which a spiral inclination angle of the spiral slit changes with respect to the spiral inclination angle on one opposed surface side of a pair of opposed surfaces constituting the spiral slit, and an abutting portion on which the stepped portion abuts when the tubular body is twisted in a direction in which the spiral of the slit is released on the other opposed surface side of the opposed surfaces; and
 a length of the stepped portion in the axial center direction is longer in a site having a first spiral inclination angle with respect to the cross-section orthogonal to the axial center direction than in a site having a second spiral inclination angle with respect to the cross-section orthogonal to the axial center direction, and wherein the first spiral inclination angle is greater than the second spiral inclination angle.

2. The medical elongated body according to claim 1, wherein a variation in the angle of the spiral slit with respect to the spiral inclination angle exceeds 90 degrees.

3. The medical elongated body according to claim 1, wherein a range of the spiral inclination angle of the stepped portion with respect to the axial center direction is within ±5 degrees.

4. The medical elongated body according to claim 1, wherein a width of a gap of the slit is constant.

5. The medical elongated body according to claim 1, wherein positions of stepped portions, which are provided in adjacent slits and are aligned in the axial center direction of the tubular body are different in a circumferential direction of the tubular body.

6. The medical elongated body according to claim 1, wherein the tubular body has a site in which the spiral inclination angle gradually changes and lengths of a plurality of stepped portions in the sites in the axial center direction gradually become longer toward the site in which the spiral inclination angle has the first angle of inclination from the site in which the spiral inclination angle has the second angle of inclination.

7. The medical elongated body according to claim 1, wherein the tubular body has a convex portion configured to protrude from one opposed surface of a pair of opposed surfaces constituting the slit, and the concave portion is configured such that the convex portion enters the other opposed surface of the opposed surfaces, and the stepped portion is configured in a part of the convex portion or the concave portion.

8. The medical elongated body according to claim 7, wherein the convex portion is configured to protrude on a side on which the spiral inclination angle of the slit becomes large, out of the distal side or the proximal side.

9. The medical elongated body according to claim 7, wherein a width of the convex portion decreases toward a direction of a protrusion of the convex portion.

10. The medical elongated body according to claim 1, wherein a site in which an angle of the slit in the stepped portion changes is configured to have a curvature.

11. The medical elongated body according to claim 1, wherein a width of a gap between opposed surfaces forming the slit is 0.01 mm to 0.05 mm.

12. The medical elongated body according to claim 1, wherein the tubular body has at least three different lengths of stepped portions.

13. The medical elongated body according to claim 1, wherein the tubular body includes a plurality of flexible portions, each of the plurality of flexible portions having a flexural rigidity, and wherein the flexural rigidity of each of the plurality of flexible portions decreases towards a distal portion of the tubular body.

14. The medical elongated body according to claim 1, wherein the tubular body includes a proximal portion without slits, and wherein the proximal portion is located proximally of the at least a part of the tubular body having the spiral slit.

15. A medical elongated body, the medical elongated body comprising:
a tubular body, at least a portion of the tubular body including a spiral slit, the tubular body including sites in which spiral inclination angles of the spiral slit in a direction of a spiral of the spiral slit with respect to a cross-section orthogonal to an axial center direction of the tubular body are different from each other, and a stepped portion in which a spiral inclination angle of the spiral slit changes with respect to the spiral inclination angle on one opposed surface side of a pair of opposed surfaces constituting the spiral slit, and an abutting portion on which the stepped portion abuts when the tubular body is twisted in a direction in which the spiral of the slit is released on the other opposed surface side of the opposed surfaces; and
a length of the stepped portion in the axial center direction is longer in a site having a first spiral inclination angle with respect to the cross-section orthogonal to the axial center direction than in a site having a second spiral inclination angle with respect to the cross-section orthogonal to the axial center direction, and wherein the first spiral inclination angle is greater than the second spiral inclination angle, the slit having a width between opposed surfaces of 0.01 mm to 0.05 mm.

16. The medical elongated body according to claim 15, further comprising:
a variation in the angle of the spiral slit with respect to the spiral inclination angle exceeds 90 degrees; and
a range of the spiral inclination angle of the stepped portion with respect to the axial center direction is within ±5 degrees.

17. The medical elongated body according to claim 15, wherein positions of stepped portions, which are provided in adjacent slits and are aligned in the axial center direction of the tubular body are different in a circumferential direction of the tubular body.

18. The medical elongated body according to claim 15, wherein the tubular body has a site in which the spiral inclination angle gradually changes and lengths of a plurality of stepped portions in the sites in the axial center direction gradually become longer toward the site in which the spiral inclination angle has the first angle of inclination from the site in which the spiral inclination angle has the second angle of inclination.

19. A medical elongated body, the medical elongated body comprising:
a tubular body having distal portion having at least a part including a spiral slit, and a proximal portion without slits, and wherein the proximal portion is located proximally of the at least a part of the tubular body including the spiral slit;
the tubular body including sites in which spiral inclination angles of the spiral slit in a direction of a spiral of the spiral slit with respect to a cross-section orthogonal to an axial center direction of the tubular body are different from each other, and a stepped portion in which a spiral inclination angle of the spiral slit changes with respect to the spiral inclination angle on one opposed surface side of a pair of opposed surfaces constituting the spiral slit, and an abutting portion on which the stepped portion abuts when the tubular body is twisted in a direction in which the spiral of the slit is released on the other opposed surface side of the opposed surfaces; and
a length of the stepped portion in the axial center direction is longer in a site having a first spiral inclination angle with respect to the cross-section orthogonal to the axial center direction than in a site having a second spiral inclination angle with respect to the cross-section orthogonal to the axial center direction, and wherein the first spiral inclination angle is greater than the second spiral inclination angle, the slit having a width between opposed surfaces of 0.01 mm to 0.05 mm.

* * * * *